(12) United States Patent
Hornbach et al.

(10) Patent No.: US 10,637,689 B2
(45) Date of Patent: Apr. 28, 2020

(54) ENDOSCOPY ARRANGEMENT WITH GALVANIC ISOLATION AND ASSOCIATED METHOD

(71) Applicant: Schölly Fiberoptic GmbH, Denzlingen (DE)

(72) Inventors: Mathias Hornbach, Waldkirch (DE); Alexander Kohler, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 16/031,287

(22) Filed: Jul. 10, 2018

(65) Prior Publication Data

US 2019/0020507 A1 Jan. 17, 2019

(30) Foreign Application Priority Data

Jul. 14, 2017 (DE) .................. 10 2017 115 887

(51) Int. Cl.
*H04B 1/38* (2015.01)
*H04L 25/02* (2006.01)
(Continued)

(52) U.S. Cl.
CPC ...... *H04L 25/0266* (2013.01); *A61B 1/00009* (2013.01); *A61B 1/00018* (2013.01); *A61B 1/00112* (2013.01); *A61B 1/00114* (2013.01); *A61B 1/00124* (2013.01); *H04L 25/0278* (2013.01); *A61B 1/04* (2013.01)

(58) Field of Classification Search
CPC ............. H04L 25/0266; H04L 25/0278; A61B 1/00018; A61B 1/00124; A61B 1/00114; A61B 1/00009; A61B 1/00112; A61B 1/04
See application file for complete search history.

(56) References Cited

U.S. PATENT DOCUMENTS 4,770,185 A * 9/1988 Silverstein ......... A61B 1/00177
600/454
5,716,323 A 2/1998 Lee
(Continued)

FOREIGN PATENT DOCUMENTS

DE 102014204065 9/2014

*Primary Examiner* — Dhaval V Patel
(74) *Attorney, Agent, or Firm* — Volpe and Koenig, P.C.

(57) ABSTRACT

To improve the quality of transmission of a signal from an image sensor to a camera controller of an endoscopy arrangement by a cable while maintaining electrical safety standards, a first circuitry arrangement used to transmit the signal within the cable includes galvanic isolation from a second circuitry arrangement used to further process the signal within the camera controller. The galvanic isolation is formed downstream of a proximal end of the cable in the signal direction, and the first circuitry arrangement has a, preferably passive, impedance matching circuit, for example arranged at the proximal end of the cable or in the camera controller. This impedance matching circuit is configured to compensate signal distortions, which arise during the transmission of the signal that is produced by the image sensor to the camera controller, preferably such that a frequency spectrum of the signal produced by the image sensor can be reproduced.

18 Claims, 1 Drawing Sheet

(51) Int. Cl.
*A61B 1/00* (2006.01)
*A61B 1/04* (2006.01)

(56) References Cited

U.S. PATENT DOCUMENTS

| | | | |
|---|---|---|---|
| 8,896,377 B1 | 11/2014 | Shrestha | |
| 9,305,193 B2 | 4/2016 | Lee et al. | |
| 9,973,940 B1 * | 5/2018 | Rappaport | H04W 16/18 |
| 2008/0204069 A1 * | 8/2008 | Ullmann | H03K 5/1252 326/21 |
| 2011/0316693 A1 * | 12/2011 | Loen | G08B 21/0219 340/539.13 |
| 2013/0150668 A1 * | 6/2013 | Kanno | A61B 1/00059 600/109 |
| 2013/0211257 A1 * | 8/2013 | Wang | A61B 18/1815 600/439 |
| 2017/0078400 A1 | 3/2017 | Binder et al. | |
| 2018/0048790 A1 * | 2/2018 | Adachi | A61B 1/00009 |

* cited by examiner

ENDOSCOPY ARRANGEMENT WITH GALVANIC ISOLATION AND ASSOCIATED METHOD

INCORPORATION BY REFERENCE

The following documents are incorporated herein by reference as if fully set forth: German Patent Application No. 102017115887.1, filed Jul. 14, 2017.

BACKGROUND

The invention relates to an endoscopy arrangement with an endoscope, which has an image sensor, and with a cable, which is configured to transmit a signal from the image sensor to a camera controller.

Further, the invention relates to the use of such an endoscopy arrangement and an associated method for transmitting signals.

Such arrangements are known, in particular for transmitting high-resolution digital video signals, produced by endoscopic camera heads, in medical applications. Here, the camera controller is typically connected to the 100-240 V mains.

The invention considers facilitating or improving a high transmission quality of image and/or video signals. At the same time, medical safety standards should be maintained.

SUMMARY

In order to solve this problem, an endoscopy arrangement having one or more features of the invention is provided. Therefore, in particular, in order to solve the problem in an endoscopy arrangement of the type set forth at the outset, the invention provides that a galvanic isolation is formed between the endoscope and a signal processing circuitry arrangement of the camera controller and that an impedance matching circuit is formed, said impedance matching circuit being arranged upstream of the signal processing circuitry arrangement of the camera controller in the signal direction. Here, the impedance matching circuit is configured to compensate changes in the form of the signal, which arise on account of the transmission.

The galvanic isolation serves to avoid, or at least reduce to a level not harmful to health, high discharge currents via the patient, as demanded by medical product standards, in the case of a faulty circuit in the camera controller, in particular an electrical short circuit, or when using faulty external devices, for example.

What the impedance matching circuit according to the invention, which, in particular, can be formed as an equalizer circuit, can achieve is that the signal form of an image and/or video signal that is transmitted by the transmission cable is substantially maintained unchanged. In particular, an edge steepness of the signal that suffices for further signal processing can be restored using the impedance matching circuit.

As a result, it is consequently possible to ensure high quality of the imaging in conjunction with the formation of a galvanic isolation. What the impedance matching circuit can further avoid in certain applications is that reflections of the signal arise in the cable, said reflections typically having a negative effect on the quality of the image transmission.

According to the invention, the problem can also be solved by further advantageous embodiments discussed below and in the claims.

According to an advantageous embodiment of the invention, provision is made for the galvanic isolation to be formed between a proximal end of the cable and the camera controller.

Unlike conventional systems, which provide a mechanically embodied galvanic isolation in the endoscope, in particular in a camera head of the endoscope, what can be achieved by forming the galvanic isolation between a proximal end of the cable and the camera controller, i.e., in particular, beyond a proximal end of the cable, is that, firstly, high electrical safety can be ensured for a patient who is examined using the endoscopic arrangement and, secondly, the camera head can have a small and compact embodiment. This is because a relatively long electrical isolation distance must typically be realized via the galvanic isolation, for example to meet legal standards for medical products; however, this can only be realized in the camera controller in the case of a desired compact structure of the camera head.

In principle, the impedance matching circuit can be arranged anywhere in the signal path between the image sensor, as the initial point, and the galvanic isolation, as the endpoint. Consequently, the impedance matching circuit can be arranged, e.g., in the endoscope, in particular in a camera head of the endoscope, or in the cable, in particular at a distal end of the cable or in the region of a proximal end of the cable, in particular in a plug, or else in, or at, the camera controller. However, it is considered advantageous in each of these cases if the impedance matching circuit is arranged upstream of the galvanic isolation in the signal direction. Thus, provision can be made for the signal to pass the impedance matching circuit before the galvanic isolation.

By way of example, the galvanic isolation can be formed on a printed circuit board within the camera controller. In this case, it is preferable if the impedance matching circuit is formed on the same printed circuit board. Consequently, it is thus possible for the impedance matching circuit and/or the galvanic isolation to be arranged downstream of an isolation point of the cable in the signal direction, in particular within the camera controller. This is advantageous in that space and material can be used efficiently.

However, the impedance matching circuit also can be arranged upstream of an isolation point of the cable in the signal direction, for example in a plug of the cable. What is advantageous in this case is that the impedance matching circuit then can be tuned exactly to the respectively employed cable. This is because each cable can have a dedicated impedance matching circuit in this case. However, the circuit must be accordingly miniaturized to this end.

In principle, the galvanic isolation, too, can be arranged upstream of an isolation point of the cable in the signal direction; for example, it also can be arranged in a plug of the cable in the case of an appropriate miniaturization.

Further, provision can be made for the impedance matching circuit to be configured in such a way that it overcompensates signal changes. This is because, particularly when arranging the impedance matching circuit in a forward part of the signal path between image sensor and camera controller, i.e., for example, in the camera head or at the distal end of the cable, it is possible also to compensate by way of an overcompensation a signal distortion that occurs in part of the signal path lying downstream of the impedance matching circuit. This is possible, even though the impedance matching circuit is arranged upstream of this rear part of the signal path.

The invention has further recognized that an overcompensation of the signal in the impedance matching circuit can also compensate signal distortions that arise during the transmission over the galvanic isolation. This applies, in particular, if the galvanic isolation is configured as an inductive coupling.

According to an advantageous configuration, provision can therefore be made for the impedance matching circuit to compensate signal changes that arise during the transmission over the galvanic isolation. To this end, in particular, a transfer function of the impedance matching circuit can be chosen in such a way that an inductance of the galvanic isolation is taken into account.

Typical cables used for transmission purposes have a response in which high-frequency components of the signal are damped more strongly than low frequency components. A further advantageous configuration therefore proposes that the impedance matching circuit damps frequency components of the signal below a threshold frequency more strongly than frequency components of the signal above the threshold frequency. Here, the threshold value frequency can be adapted to a response of the cable, according to which frequency components below the threshold value frequency are damped less strongly in the cable than frequency components above the threshold value frequency. Therefore, in particular, the threshold frequency can be a cutoff frequency of the cable.

Consequently, in a frequency range required for the transmission of the signal, the impedance matching circuit can exhibit a transfer function that corresponds to a high-pass characteristic. Here, the impedance matching circuit can exhibit a transfer function that corresponds to a band pass filter in a frequency range that goes beyond this required frequency range. By way of example, if the circuit is embodied on a printed circuit board, a low-pass characteristic of the printed circuit board can be overlaid on the high-pass characteristic of the impedance matching circuit, and so a band pass response arises overall.

In particular, the cutoff frequency of the cable can be a frequency below which signal components are damped by at least 3 dB during the transmission through the cable. Since the level of the damping typically depends on the length of the cable used, it is preferable for the impedance matching circuit to be designed for a predetermined length of the cable. Preferably, this length can be approximately 2.5 to 4.5 m. However, matching to other cable lengths is also realizable, for example to 5 m or longer. Consequently, it is possible to ensure that cables with different lengths can be used with the endoscopy arrangement with an unchanging high quality of the image transmission, wherein the impedance matching circuit should be matched accordingly.

A further preferred embodiment according to the invention provides for DC voltage components of the signal to be transmittable by the impedance matching circuit. Thus, the impedance matching circuit preferably can be embodied in such a way that even frequencies down to 0 Hz are passed. What is advantageous here is that even low frequency components, in particular DC components, of the signal can be transmitted to the camera controller. By way of example, this is advantageous for the transmission of video signals as signal pauses that have to be transmitted for subsequent error-free representation may be present therein between individual lines of a video image; moreover, the retrieval of associated synchronization signals may be made easier. In certain applications, the transmission of DC components may even be mandatory.

According to an embodiment of the invention, the impedance matching circuit has a transfer function that corresponds to a high-pass filter, preferably a $1^{st}$ order high-pass filter, over a frequency range that is used for the signal transmission. Here, a limit frequency of the transfer function can be equal to or less than a, or the, above-described cutoff frequency of the cable, in particular. Hence, a specific embodiment with which the above-described compensation of changes in the signal form during the transmission by the cable can be realized is specified.

According to an embodiment that is suitable for the transmission of video signals, it already suffices if the impedance matching circuit is configured to transmit frequency components of the signal below 75 MHz.

According to further embodiments that are advantageous, in particular for transmitting video signals with a high image quality and a high resolution, the impedance matching circuit can be designed for a signal bandwidth of at least 1.5 GHz, preferably at least 2.0 GHz, particularly preferably of at least 3.0 GHz. In particular, a resonant width of the impedance matching circuit to this end can be equal to or greater than a bandwidth of the signal. As result of the design of the impedance matching circuit for signal bandwidths of more than 1.5 GHz, it becomes possible, in particular, to apply so-called "scrambling" and "descrambling" methods. Using these methods, a signal to be transmitted can be distributed on a frequency band in order to facilitate a transmission of large amounts of data that is as broadband and hence as quick as possible.

According to the invention, it is particularly advantageous if the cable and the impedance matching circuit are chosen and/or embodied in such a way that a signal transfer function that is set by the cable and the impedance matching circuit has an unchanging or largely unchanging transfer quotient. Here, it is preferable for the transfer quotient to remain the same or largely the same over an entire signal bandwidth used for transmission purposes. By way of example, the transfer quotient can be specified as the quotient of an input and output signal amplitude or as a quotient of an input and output phase. This specific embodiment renders it possible to ensure that the signal produced by the image sensor can be transmitted to the camera controller with as little falsification as possible. In particular, it is consequently possible to transmit steep edges of the signal virtually without change, which is advantageous, in particular, when using digital signals in order to facilitate a robust signal transmission.

By way of example, if the invention is applied to the transmission of a digital video signal with a bandwidth of 1.5 GHz, it is consequently possible to obtain a transfer function from a camera head of the endoscope to the galvanic isolation which achieves unchanging damping or largely unchanging damping over the entire frequency range of the signal such that the signal form is maintained substantially without change.

According to the invention, a particularly compact endoscopy arrangement can be achieved when the impedance matching circuit is arranged in the cable, in particular in a plug at the proximal end of the cable, or in, or at, the camera controller.

In general, the invention considers it advantageous if the impedance matching circuit is disposed upstream of the galvanic isolation such that the signal passes the impedance matching circuit before the galvanic isolation. This is because the impedance matching circuit, for example, can be formed in the cable itself, in particular as described above, in the case of such an embodiment. If cables of different length are intended to be used, each of the cables can have a dedicated impedance matching circuit that is expressly matched to the specific cable length, and so a best possible signal quality always can be ensured after the transmission through the respective cable.

Particularly in the case of an impedance matching circuit that is disposed upstream of the galvanic isolation, provision can be made for the impedance matching circuit to be realized using passive components only. Thus, the impedance matching circuit can be realized as a passive equalizer circuit. Due to dispensing with active electronic components, as are comprised by active impedance matching circuits, there is no need for an additional voltage supply for the impedance matching circuit. This simplifies the design of the endoscopy arrangement overall. In relation to the otherwise known active adaptation circuits, a passive circuit further is advantageous in that its response is precisely known, whereas, as a rule, active circuits, which typically have to be additionally purchased, are not precisely understandable in terms of their control system response.

Moreover, the invention has recognized that better results in the quality of the signal transmission can be obtained by forming the impedance matching circuit from passive components or as a passive equalizer circuit in comparison with the use of active circuits, such as signal processing ICs, for example, since passive components or circuits are typically less susceptible to reflected signals. The use of a passive impedance matching circuit, in particular at the distal end of the cable, is therefore advantageous in that unwanted reflections, which are transmitted or input coupled from proximal to distal via the galvanic isolation and the cable, are better controllable or better suppressible.

On account of the damping exerted by means of the impedance matching circuit on certain frequency components of the signal, it can be advantageous, particularly in the case of a long cable length, if an active signal gain is formed. In particular, this can be disposed downstream of the galvanic isolation. Consequently, a signal with a sufficient amplitude for further processing can be provided by means of the signal gain. An amplifier can be provided for employment of the signal gain. By way of example, said amplifier can be arranged in the CCU and/or be supplied with electrical voltage by the latter.

Alternatively, or in a complementary manner, provision can further be made for an amplifier, in particular a further amplifier, to be provided, the latter amplifying the signal prior to it passing the galvanic isolation. What is advantageous here is that the integrity and the noise immunity of the signal during the transmission over the galvanic isolation can be improved.

Particularly in the case of chip-in-tip endoscopes, i.e., endoscopes in which an image sensor is arranged in a distal end region of an endoscope shaft, there already can be a significant signal path within the endoscope, for example from the image sensor to a proximally arranged head or handle of the endoscope. Signal distortions may already arise within the endoscope along such a signal path, i.e., still before the transmission through the cable to the camera controller.

In order to be able to already largely compensate such changes in the signal form first, one embodiment of the invention provides that a further impedance matching circuit is formed. By way of example, the latter can be formed in the endoscope, in particular in a camera head of the endoscope, or in the cable. Here, this further impedance matching circuit can be configured, in particular, to compensate changes in the form of the signal that already arise prior to the transmission thereof through the cable.

For the further impedance matching circuit, too, provision can further be made for the latter to overcompensate signal changes. Using this, it is possible to obtain the advantages described at the outset. By way of example, this can also compensate a deviating cable length, to which a first impedance matching circuit in the camera controller alone is only matched insufficiently.

Consequently provision can be made according to a specific embodiment for a first impedance matching circuit to be arranged spatially separated, in particular spatially separated by the cable, from a second impedance matching circuit. By way of example, the first impedance matching circuit can be arranged in the camera controller and the second impedance matching circuit can be arranged in the camera head.

The invention has further recognized that it is advantageous if the signal to be transmitted from the endoscope to the camera controller is a digital signal, in particular with a signal form known per se. This is because the reconstruction of a video signal at the proximal end of the cable with the aid of passive components of the impedance matching circuit, for example, is particularly successful in this case as the requirements on the fidelity of the signal form are lower in comparison with the use of analog signals. By way of example, as a rule, it is sufficient to reliably detect the level change in a digital signal, for the purposes of which, substantially, a good edge steepness is required; the latter can be restored with an impedance matching circuit according to the invention.

Particularly for medical applications, but also for other applications, it is advantageous if the cable and/or the impedance matching circuit has a ground-potential-free shielding. Such shielding is sometimes also referred to as "floating ground"; it can serve to suppress the emission and/or input coupling of RF signals. Here, a preferred embodiment provides for the shielding to be coupled to an electric ground potential line, preferably of the camera controller, by a coupling capacitance, preferably a high-voltage-resistant coupling capacitance. In particular, high-frequency noise in the signal is suppressible by means of the coupling capacitance.

According to a further advantageous embodiment, the galvanic isolation can be formed as an inductive coupling. By embodying the galvanic isolation as an inductive coupling, it is possible to achieve a higher noise immunity, particularly in comparison with galvanic isolations embodied in a capacitive fashion, since high-frequency noise sources, in particular, can be suppressed more strongly, unlike in the case of capacitive coupling.

Here, it is preferable if the inductive coupling has a low number of turns. In this case, in particular, a low number of turns per unit length can mean that less than 5 turns, preferably less than 3 turns, in particular 1.25 turns are formed for inductive signal transmission. Here, it is particularly preferred if the number of turns per unit length of the inductive couplings have the same embodiment on the primary and secondary side. Here, the "secondary side" denotes the turns that are arranged proximally in relation to the galvanic isolation. What such embodiments can ensure, in particular, is that a parasitic capacitance arising on account of the galvanic isolation is small in relation to a capacitance of a, or the, above-described coupling capacitor, by means of which a, or the, above-described shielding of the cable and/or of the impedance matching circuit is coupled to an electrical ground potential line.

In medical applications, it can be particularly advantageous if the inductive coupling is designed in such a way that the just described parasitic capacitance is less than 15 pF. This is because the discharge currents that are discharged by the parasitic capacitance are negligibly small in the case of such a low capacitance.

A further preferred embodiment provides for the cable to be formed as a coaxial cable or as a line with at least two wires, preferably with shielding. In the case of the two-wire form of the cable, for example in the form of twin axial line, it is advantageous if a separate impedance matching circuit is provided for each of the at least two wires. However, it is also possible to provide a combined, differential circuit element which compensates the at least two wires together or in combined fashion. What such embodiments can achieve, in particular, is that digital video signals with a high resolution can be transmitted using standardized video transfer protocols.

The cable used for the signal transmission further can have lines for low-frequency signals. By way of example, the cable can provide a voltage supply for the camera head or an RS-232 line for transmitting commands from the camera controller to the camera head.

According to the invention, the features of the coordinate independent claim directed to the use are provided to solve the problem set forth at the outset. In particular, it is consequently proposed that an endoscopy arrangement according to the invention, in particular as described above and/or as claimed in any one of the claims directed to an endoscopy arrangement, is used to transmit an image or video signal, preferably a digital image or video signal.

For the purposes of increasing the quality of the image transmission, it may be advantageous if the image or video signal is matched by means of "scrambling" to a bandwidth that is usable for transmission purposes prior to the transmission through the cable. By means of a "scrambling" method, known per se, it is possible, in particular, to modify and/or interchange bit arrays of the signal prior to the transmission through the cable. By way of example, this renders it possible to better exploit a bandwidth that is available for signal transmission purposes.

Further, according to the invention, the features of the independent method claim are provided for solving the problem specified at the outset. In particular, according to the invention, in a method for transmitting signals, in particular image or video signals, by a cable from an image sensor to a camera controller, in particular of an endoscopy arrangement as described above and/or as claimed in any one of the claims directed to an endoscopy arrangement, what is consequently provided for the purposes of solving the problem is that the signal, after transmission through the cable, is prepared by an impedance matching circuit, in particular as described above. What is advantageous in this method is that an original edge steepness of the signal can be at least partly restored. This can ensure a particularly robust transmission, in particular of high-resolution video images.

BRIEF DESCRIPTION OF THE DRAWINGS

The invention will now be described in more detail on the basis of exemplary embodiments, without it being restricted to these embodiments.

Further exemplary embodiments emerge by combining the features of individual claims or a plurality of claims among themselves and/or with individual features or a plurality of features of the respective exemplary embodiment. In particular, it is possible to obtain embodiments of the invention from the subsequent description of a preferred exemplary embodiment in conjunction with the general description, the claims and the drawings.

Figure 1:
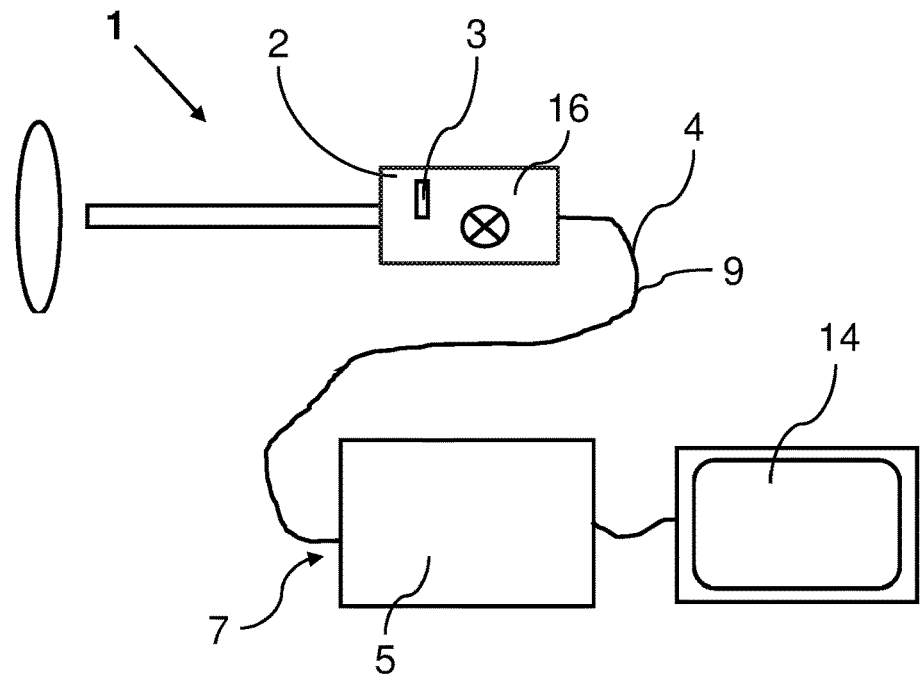
Figure 2:
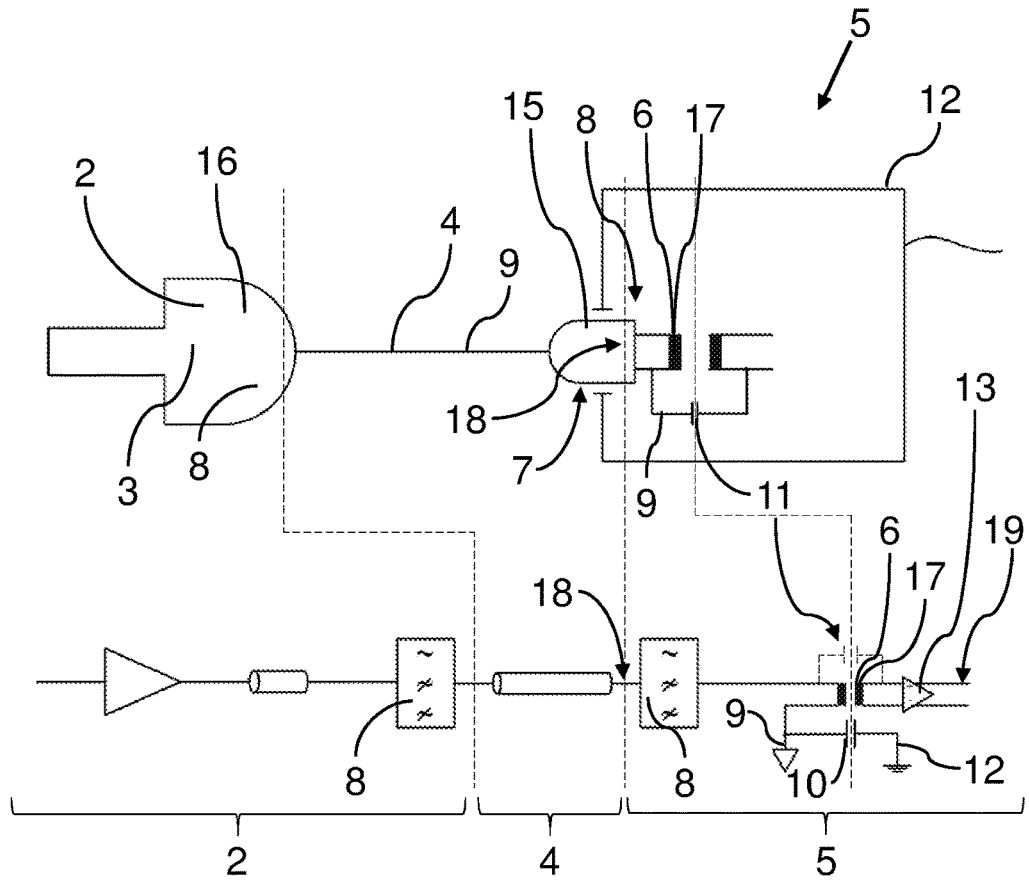

In detail:

FIG. 1 shows an overview of an endoscopy arrangement according to the invention, FIG. 2 shows a very schematic illustration of the endoscopy arrangement from FIG. 1, in conjunction with an associated electrical circuit diagram of the endoscopy arrangement (lower half of FIG. 2).

DETAILED DESCRIPTION

FIG. 1 shows an endoscopy arrangement denoted by 1 overall. It includes an endoscope 2, which has a camera head 16 with an image sensor 3 and which is connected to a camera controller 5 by means of a coaxial cable 4. Via the cable 4, a digital video signal generated by the image sensor 3 can be transmitted from the endoscope 2 to the camera controller 5 in order to subsequently be presented on a monitor 14.

As shown in FIG. 2, the cable 4 is connected by a plug 15 at the proximal end 7 of the cable 4 to the camera controller 5 via an isolation point 18. In the signal direction downstream of the plug 15 or the isolation point 18, a galvanic isolation 6 is arranged between the proximal end 7 of the cable 4 and the camera controller 5 as an inductive coupling 17. Due to this inductive coupling 17, there is a parasitic capacitance 11 of approximately 11 pF between a circuit of the cable 4, or a first impedance matching circuit 8 formed downstream of the plug 15 in the signal direction, on the primary side and a signal processing circuitry arrangement 19 of the camera controller 5 on the secondary side.

In the exemplary embodiment shown in FIG. 2, the first impedance matching circuit 8 is arranged on a printed circuit board within the camera controller 5, together with the inductive coupling 17. As shown by the electrical circuit diagram in the lower half of FIG. 2, a coupling capacitance 10 is formed, the latter coupling a shielding 9 of the cable 4 to an electric ground potential line 12 of the camera controller 5.

The coupling capacitance 10 has high-voltage resistance and, with approximately 233 pF, a substantially higher capacitance than the parasitic capacitance 11. As a result of this embodiment, it is firstly possible to efficiently suppress high-frequency noise, which couples into the shielding 9 of the cable 4, by discharge to ground (ground potential 12). Secondly, by restricting the parasitic capacitance 11, a discharge current that possibly occurs is substantially determined by the known coupling capacitance 10 and therefore reliably controllable.

Following the electrical circuit diagram of FIG. 2 from left to right, the video signal generated by the image sensor 3 initially passes an electric line within the camera head 16 of the endoscope 2. The signal distortions occurring in the process are compensated by a second impedance matching circuit 8 within the camera head 16 of the endoscope 2.

Subsequently, the restored signal passes through the cable 4 up to the plug 15 of the proximal end 7 of the cable 4. Due to the response of the cable, there are further changes in the signal form on this transmission path along the cable 4. These changes are compensated by the first impedance matching circuit 8, already described above, which is formed within the camera controller 5 and disposed upstream of the galvanic isolation 6 from a circuitry point of view.

Consequently, a largely restored signal is present at the primary side of the inductive coupling 17. This restored signal is transmitted over the galvanic isolation 6. After passing the galvanic isolation 6, the signal can then be actively amplified with the aid of the downstream amplifier 13, as illustrated in FIG. 2, before said signal is supplied to a signal-processing circuitry arrangement 19 of the camera controller. In the example illustrated in FIG. 2, the impedance matching circuit 8 is therefore arranged still upstream in the signal direction of this signal-processing circuitry arrangement of the camera controller (5).

According to a further advantageous embodiment, provision can be made, as an alternative or in addition thereto, for the signal to be actively amplified already prior to the passage of the galvanic isolation, i.e., on the primary side of the inductive coupling 17, for example with the aid of a second amplifier (not shown in FIG. 2).

The compensation provided by the first impedance matching circuit 8, which is arranged within the camera controller 5, is achieved by virtue of frequency components of the signal below a threshold frequency being damped more strongly than frequency components of the signal above the threshold frequency. Here, the cutoff frequency of the cable 4, which has a length of 3.5 m in the present exemplary embodiment, is selected as the threshold frequency. Here, passive components only are used to obtain the frequency-dependent damping of the signal caused by the impedance matching circuit.

Using an endoscopy arrangement 1 as shown in FIG. 2, it is possible to reliably transmit digital video signals with bandwidths of more than 3.0 GHz without information loss from the camera head 16 to the camera controller 5 via the coaxial cable 4 while, at the same time, the endoscope 2 remains galvanically isolated from the camera controller 5 such that the standards relating to electrical safety of the endoscopy arrangement 1 can be observed.

In summary, so as to improve the quality of the transmission of a signal, in particular an image or video signal, from an image sensor 3 to a camera controller 5 of an endoscopy arrangement 1 by a cable 4 while maintaining electrical safety standards, it is provided that a first circuitry arrangement that is used to transmit the signal within the cable 4 is embodied with galvanic isolation from a second circuitry arrangement 19 that is used to further process the signal within the camera controller 5. To this end, in particular, a galvanic isolation 6 can be formed, preferably downstream of a proximal end 7 of the cable 4 in the signal direction, particularly preferably as an inductive coupling 17.

Further, it is provided that the first circuitry arrangement has an impedance matching circuit 8, preferably with a passive embodiment, for example arranged at the proximal end 7 of the cable 4 or in the camera controller 5, said impedance matching circuit being configured to compensate signal distortions, which arise during the transmission of the signal that is produced by the image sensor 3 to the camera controller 5, preferably in such a way that a frequency spectrum of the signal that is produced by the image sensor 3 can be reproduced (see FIG. 2).

LIST OF REFERENCE SIGNS

1 Endoscopy arrangement
2 Endoscope
3 Image sensor
4 Cable
5 Camera controller
6 Galvanic isolation
7 Proximal end (of the cable)
8 Impedance matching circuit
9 Shielding
10 Coupling capacitance
11 Parasitic capacitance
12 Ground potential line
13 Amplifier
14 Monitor
15 Plug
16 Camera head
17 Inductive coupling
18 Isolation point (of the cable)
19 Signal-processing circuitry arrangement

The invention claimed is:

1. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and
the impedance matching circuit damps frequency components of the signal below a threshold frequency more strongly than frequency components of the signal above the threshold frequency.

2. The endoscopy arrangement as claimed in claim 1, wherein the galvanic isolation is formed between a proximal end of the cable (4) and the camera controller.

3. The endoscopy arrangement as claimed in claim 1, wherein the impedance matching circuit is arranged upstream of the galvanic isolation in the signal direction, such that the signal passes the impedance matching circuit before the galvanic isolation.

4. The endoscopy arrangement as claimed in claim 1, wherein the impedance matching circuit at least one of overcompensates changes in the signal or compensates changes in the signal that arise during the signal transmission over the galvanic isolation.

5. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and
DC voltage components of the signal are transmittable by the impedance matching circuit.

6. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and the impedance matching circuit has a transfer function over a frequency range used for signal transmission that corresponds to a high pass filter such that a frequency limit of the transfer function is equal to or less than a cutoff frequency of the cable.

7. The endoscopy arrangement as claimed in claim 1, wherein the impedance matching circuit is designed for transmitting frequency components of the signal that are at least one of below 75 MHz or for a signal bandwidth of at least 1.5 GHz.

8. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and
the cable and the impedance matching circuit are embodied such that a signal transfer function that is set by the cable and the impedance matching circuit has an unchanging or largely unchanging transfer quotient over an entire signal bandwidth used for transmission purposes.

9. The endoscopy arrangement as claimed in claim 1, wherein the impedance matching circuit is arranged in the endoscope, in the cable (4), or in or at the camera controller.

10. The endoscopy arrangement as claimed in claim 1, wherein the impedance matching circuit comprises passive components only or is a passive equalizer circuit, or both.

11. The endoscopy arrangement as claimed in claim 1, further comprising at least one of an amplifier which amplifies the signal prior to passing the galvanic isolation or an active signal gain disposed downstream of the galvanic isolation.

12. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and
a further impedance matching circuit formed in the endoscope or in the cable, said further impedance matching circuit being configured to compensate changes in a form of the signal that already arise prior to transmission of the signal thereof through the cable, or the impedance matching circuit is arranged spatially separated from a second impedance matching circuit.

13. The endoscopy arrangement as claimed in claim 1, wherein the signal is a digital signal.

14. The endoscopy arrangement as claimed in claim 1, wherein at least one of the cable or the impedance matching circuit has a ground-potential-free shielding.

15. An endoscopy arrangement comprising:
an endoscope, which has an image sensor,
a camera controller having signal processing circuitry,
a cable, which is configured to transmit a signal from the image sensor to the camera controller,
a galvanic isolation formed between the endoscope and the signal processing circuitry of the camera controller,
an impedance matching circuit configured to compensate changes in a form of the signal which arise due to the signal transmission, the impedance matching circuit is arranged upstream of the signal processing circuitry arrangement of the camera controller in the signal direction, and
the galvanic isolation is embodied as an inductive coupling, and a parasitic capacitance arising due to the galvanic isolation is small in relation to a capacitance of a coupling capacitor, by which a shielding of the cable is electrically coupled to the camera controller.

16. The endoscopy arrangement as claimed in claim 1, wherein the cable is formed as a coaxial cable or as a line with at least two wires, and separate ones of the impedance matching circuit are provided for each of the at least two wires.

17. A method for using an endoscopy arrangement as claimed in claim for transmitting an image or video signal, the method comprising:
providing the endoscopy arrangement including an endoscope, which has an image sensor, a camera controller having signal processing circuitry, a cable, which is configured to transmit a signal from the image sensor to the camera controller, a galvanic isolation formed between the endoscope and the signal processing circuitry of the camera controller, an impedance matching circuit configured to compensate changes in a form of the signal which arise due to the signal transmission, the impedance matching circuit is arranged upstream of the signal processing circuitry arrangement of the camera controller in the signal direction,
matching the image or video signal by scrambling to a bandwidth that is usable for transmission purposes prior to the transmission through the cable, and
at least one of modifying or interchanging bit arrays of the signal prior to the transmission through the cable.

18. The endoscopy arrangement as claimed in claim 1, wherein the threshold frequency is a cutoff frequency of the cable, and the impedance matching circuit is designed for a predetermined length of the cable.

* * * * *